US012411276B2

(12) United States Patent
Pal (10) Patent No.: US 12,411,276 B2
(45) Date of Patent: Sep. 9, 2025

(54) ANNULAR LIGHT SOURCE DEVICE FOR FUNDUS CAMERAS (71) Applicant: FORUS HEALTH PVT. LTD., Bangalore (IN)

(72) Inventor: Sourav Pal, Bangalore (IN)

(73) Assignee: FORUS HEALTH PVT. LTD. (IN)

( * ) Notice: Subject to any disclaimer, the term of this patent is extended or adjusted under 35 U.S.C. 154(b) by 496 days.

(21) Appl. No.: 17/791,490

(22) PCT Filed: Mar. 4, 2021

(86) PCT No.: PCT/IN2021/050204
§ 371 (c)(1),
(2) Date: Jul. 7, 2022

(87) PCT Pub. No.: WO2021/176471
PCT Pub. Date: Sep. 10, 2021

(65) Prior Publication Data
US 2023/0039680 A1 Feb. 9, 2023

(30) Foreign Application Priority Data

Mar. 4, 2020 (IN) .............................. 202041009258

(51) Int. Cl.
A61B 3/10 (2006.01)
A61B 3/00 (2006.01)
A61B 3/12 (2006.01)
A61B 3/14 (2006.01)
F21V 8/00 (2006.01)
G02B 19/00 (2006.01)

(52) U.S. Cl.
CPC .......... *G02B 6/0001* (2013.01); *A61B 3/0008* (2013.01); *A61B 3/12* (2013.01); *A61B 3/14* (2013.01); *G02B 19/0047* (2013.01)

(58) Field of Classification Search
CPC .......... A61B 3/0008; A61B 3/12; A61B 3/14; G02B 6/0001; G02B 19/0047
USPC .............................. 351/206, 221; 362/249.02
See application file for complete search history.

(56) References Cited

U.S. PATENT DOCUMENTS 7,529,445 B2 * 5/2009 Ikeda ................... H04N 1/0318
362/628
8,974,060 B2 3/2015 Plaian
2012/0050683 A1 3/2012 Yates

FOREIGN PATENT DOCUMENTS

EP 2093482 A2 8/2009
WO WO-2006016366 A2 * 2/2006 ............... A61B 3/12
WO WO-2010091998 A1 * 8/2010 ............... F21V 5/04

* cited by examiner

Primary Examiner — Mahidere S Sahle (57) ABSTRACT

A device has a light guide portion and a light collector portion. The light guide portion is cup shaped. The wall of the cup has a cross section defined by sections of two ellipses disposed in a predefined manner with each other. The light collector portion is also cup-shaped, inverted with reference to the light guide portion, by a section of an ellipse and straight lines defined with reference to the light guide portion. The device radiates an annular illumination at the rim of the cup through total internal reflection of light from an LED, collected by the light collector portion. The device is made of a clear, colourless, substantially transparent material by injection moulding, one example being Polycarbonate. An annular light source system and a fundus camera using such a system are also disclosed.

13 Claims, 7 Drawing Sheets

Prior art

ANNULAR LIGHT SOURCE DEVICE FOR FUNDUS CAMERAS

TECHNICAL FIELD

This disclosure belongs to the field of ophthalmic diagnostic devices and in particular to the field of light sources used in ophthalmic diagnostic devices.

BACKGROUND

Fundus photography involves photographing the posterior segment of an eye; also known as the fundus. Specialized fundus cameras consisting of an imaging system attached to a flash enabled camera are used in fundus photography. Some fundus cameras use an annular light source, instead of a point source, for its operation because an annular illumination offers certain advantages in its use.

There are multiple known means for producing an annular light source. One way is to use a light source and mask the central area of a disk like illumination surface to produce an annular light beam. Some use a light guide annular light source device. They have; however, certain disadvantages.

For example, the granted U.S. Pat. No. 8,974,060 B2 describes a device having an arrangement using LEDs to produce a ring light source. It provides a lighting device comprising a light concentrator device associated with a light source comprising a plurality of LED devices. The light concentrator device is composed of a solid transparent body, comprising: a first surface at which a light input section is defined to receive the light radiation emitted by the light source and a second surface at which a light output section is defined to transmit a light beam having a ring shape, and a plurality of protrusions that protrude from said first surface, at the light input section, said protrusions acting as collimation lenses of the light radiation coming from said light source; and a plurality of reflection surfaces of the light radiation received from said light input section, said protrusions and said reflection surfaces being mutually positioned so as to convey the light radiation coming from said light source along a predefined path, which extends internally to said transparent body, between said light input section and said light output section.

The device mentioned above, and other such devices known in the art have one or more drawbacks. They are difficult to manufacture. They are difficult to assemble in a fundus camera. They use multiple light sources and often consume a large amount of power. This also leads to heating of the fundus camera system which thus needs cooling arrangements. The complex shape of the components and the multiple light sources of light along with the cooling means make the whole camera heavy and complex in construction.

SUMMARY

This summary is provided to introduce a selection of concepts in simple manners that are further described in the detailed description of the disclosure. This summary is not intended to identify key or essential inventive concepts of the subject matter nor is it intended to determine the scope of the disclosure.

Thus, there is a need for an annular light source that overcomes at least one of the drawbacks of the present state of the art annular light sources. It is preferable to have a light source that is easy to manufacture. It is preferable to have a light source that is easy to assemble in a Fundus camera. It is preferable to have a light source device of light weight with low power consumption and does not need external cooling.

In order to solve at least one of the problems mentioned above, the present disclosure discloses a light guide device having a cup shaped light guide portion and an inverted cup shaped light receiving portion made of a transparent material suitable for making an effective light guide.

The disclosed light guide device is made by injection moulding, for example. Due to the simple shape of the device, the device is easy to manufacture and also easy to assemble into a fundus camera. Further, the disclosed device is configured for using a single LED as its light source.

Thus, disclosed is light guide device, for producing annular illumination, the device comprising a light guide portion characterised by having substantially the shape of a cup formed by a wall made of a substantially transparent material, wherein, the wall having a cross section defined by a Cartesian plane and with reference to Cartesian x-axis and y-axis and origin, the cross section having an outer contour and an inner contour, the outer contour of the wall being a section of a first ellipse with its major axis being parallel to the y-axis with a centre of the ellipse displaced along the x-axis by a first predetermined distance, wherein a ratio of a length of a major axis and a length of a minor axis of the first ellipse is a first predetermined number, the inner contour of the wall being a section of a second ellipse with its major axis forming a first predetermined angle with the x-axis and intersecting the y-axis at a second predetermined distance from the origin and wherein a ratio of a length of a major axis and a minor axis of the second ellipse is a second predetermined number, the inner contour spanning a line parallel to the x-axis at a third predetermined distance and the intersection of the inner contour and the y-axis, the outer contour spanning the line parallel to the x-axis at the third predetermined distance and an intersection of the outer contour and a line parallel to the x-axis at a fourth predetermined distance from the origin, and an annular light portion defined by a straight line spanning the points of intersection of the outer and inner contour and the line parallel to the x-axis at a third predetermined distance.

It is to be noted that the cup shape of the light guide can be visualised in three dimensions by rotating the above described cross section around the y-axis of the defined Cartesian coordinate system.

Further, the light guide device has a light collector part which collects the light from an LED placed at a predefined position. It is to be noted that the description of the light collector part as described herein is similar to the description of the light guide portion. The inverted cup shape can be defined by defining a cross section forming the inverted cup. Even though this portion has been described separately for ease of understanding it is to be noted that the cup shaped light guide portion and the inverted cup shaped light collector portion together form the integrated annular light source disclosed herein.

The light collector portion of the light guide device is as follows. The light guide device described above comprises a light collector portion for collecting a light emitted by a light source, The light guide device of claim 1 comprising a light collector portion for collecting a light emitted by a light source, the light collector portion having a shape of an inverted cup integral with the light guide device, wherein the cross section of a wall of the inverted cup is characterised by, a contour of an inner surface of the inverted cup proximal to the origin being a section of a third ellipse with its major axis parallel to the x-axis, with the centre of the third ellipse lying on the y-axis at a fifth predetermined distance from the origin and spanning a point of intersection of the third ellipse and the y-axis and the line parallel to the x-axis at the fourth predetermined distance, the ratio of a length of a major axis and a length of a minor axis of the third ellipse being a third predetermined number, an inner contour of the cross section of the inverted cup being a part of a straight line intersecting the y-axis at a sixth predetermined distance from the origin at a second predetermined angle with the y-axis, and extending between a point of intersection with the section of the third ellipse a point of intersection with a line parallel to the x-axis at a seventh predetermined distance from it, and the outer contour of the inverted cup being a straight line parallel to the y-axis, spanning a point of intersection of the line parallel to the x-axis at a fourth predetermined distance from it and the outer contour of the light guide.

It is to be noted that the description above describes a device with two portions and the two portions are formed or manufactured as a single integrated whole. The light collector part described can be thought of as minimum configuration required to work effectively to collect the light emitted be light source and through the light guide part, emit light in the shape of an annular ring, through total internal reflection. Thus, minor modifications may occur to a person of ordinary skill in the art to suit engineering requirements such as assembly into an ophthalmic instrument. Such modification may include narrowing down the width or diameter of the light collector part or adding a disc like extension to the light collector part or any other suitable modification without substantially affecting the functioning of the light collector and light guide portions of the disclosed device. All such variants are deemed to be a part of the device disclosed herein.

The summary above is illustrative only and is not intended to be in any way limiting. Further aspects, exemplary embodiments, and features will become apparent by reference to the drawings and the following detailed description.

BRIEF DESCRIPTION OF THE FIGURES

The disclosure will be described and explained with additional specificity and detail with the accompanying figures in which.

Further, persons skilled in the art to which this disclosure belongs will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those of ordinary skill in the art having the benefit of the description herein.

DETAIL DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications to the disclosure, and such further applications of the principles of the disclosure as described herein being contemplated as would normally occur to one skilled in the art to which the disclosure relates are deemed to be a part of this disclosure.

It will be understood by those skilled in the art that the foregoing general description and the following detailed description are exemplary and explanatory of the disclosure and are not intended to be restrictive thereof.

The terms "comprises", "comprising", or any other variations thereof, are intended to cover a non-exclusive inclusion, such that a process or method that comprises a list of steps does not include only those steps but may include other steps not expressly listed or inherent to such a process or a method. Similarly, one or more devices or sub-systems or elements or structures or components preceded by "comprises . . . a" does not, without more constraints, preclude the existence of other devices, other sub-systems, other elements, other structures, other components, additional devices, additional sub-systems, additional elements, additional structures, or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this disclosure belongs. The system, methods, and examples provided herein are illustrative only and not intended to be limiting.

Embodiments of the present disclosure will be described below in detail with reference to the accompanying figures.

Embodiments of the present disclosure provide a light guide device for generating an annular illumination source. The following is a brief description of an exemplary fundus camera 100, using an annular light source and is provided for an understanding of its purpose and function, with reference to FIG. 2. 101, which is not a part of the fundus camera, represents a dark screen illuminated at its centre by a ring shaped light. The ring shaped light is referred to hereinafter as an annular light beam produced by an annular light source device. A subject undergoing ophthalmological examination is positioned in front of the fundus camera. The eye 105 of the subject is so positioned that an annular light beam falls on the cornea of the eye 105. An annular light source 120 produces an annular beam of light. Even though what is being described here is a generic fundus camera, the annular light source 120 is shown here as the disclosed annular light source device. An optical system comprising lenses 110 and 115 and a beam splitter 130 redirects the annular light beam on to the eye 105. The annular light beam forms an annular image on the cornea of the eye 105. The annular light falling on the cornea of the eye 105 is focused by the optical system. This annular light beam passes through the iris of the eye 105 and illuminates the retina uniformly. This uniformly illuminated retina enables a digital camera 140 to capture a detailed picture of the retina, suitable for diagnostic purposes. The optical system comprising lenses 110 and 135 and beam splitter 130 focuses the light reflected by the retina of the eye 105 on to the digital camera 140. An operator of the fundus camera 100 views the reflected light from the retina of the eye 105 through a view finder of the digital camera 140, if one is provided. Alternatively, the image as received by the digital camera 140 is communicated to an external screen for viewing by the operator and to make necessary adjustments in focusing to capture a clear picture of the retina. Additionally, the optical system may also have a mask 125, with an annular gap, for reducing any stray light other than that from the annular beam from the annular light source 120 from reaching the eye 105.

Figure 1:
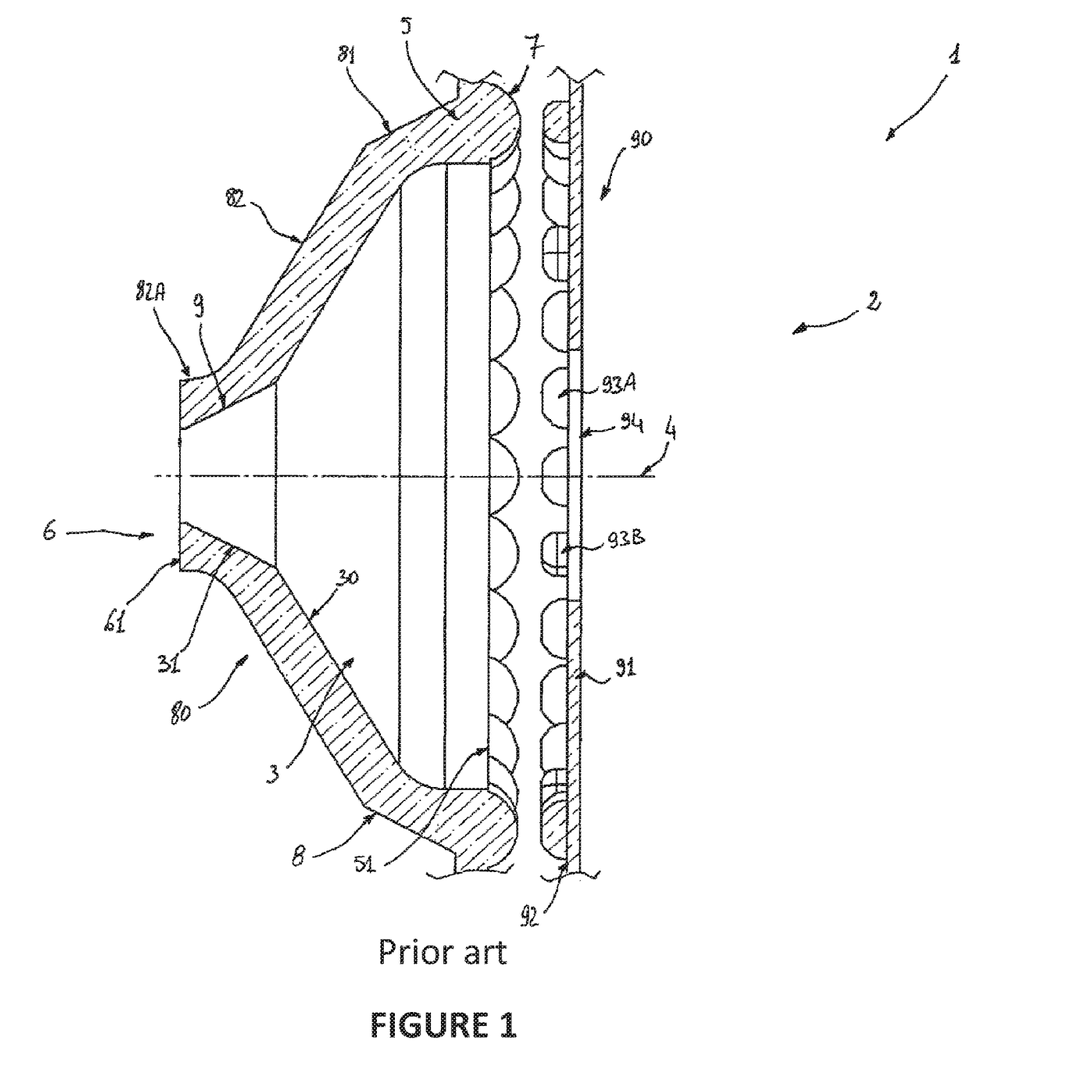
FIG. 1 shows a prior art ring light generating device, according to one embodiment of the present disclosure.
Figure 2:
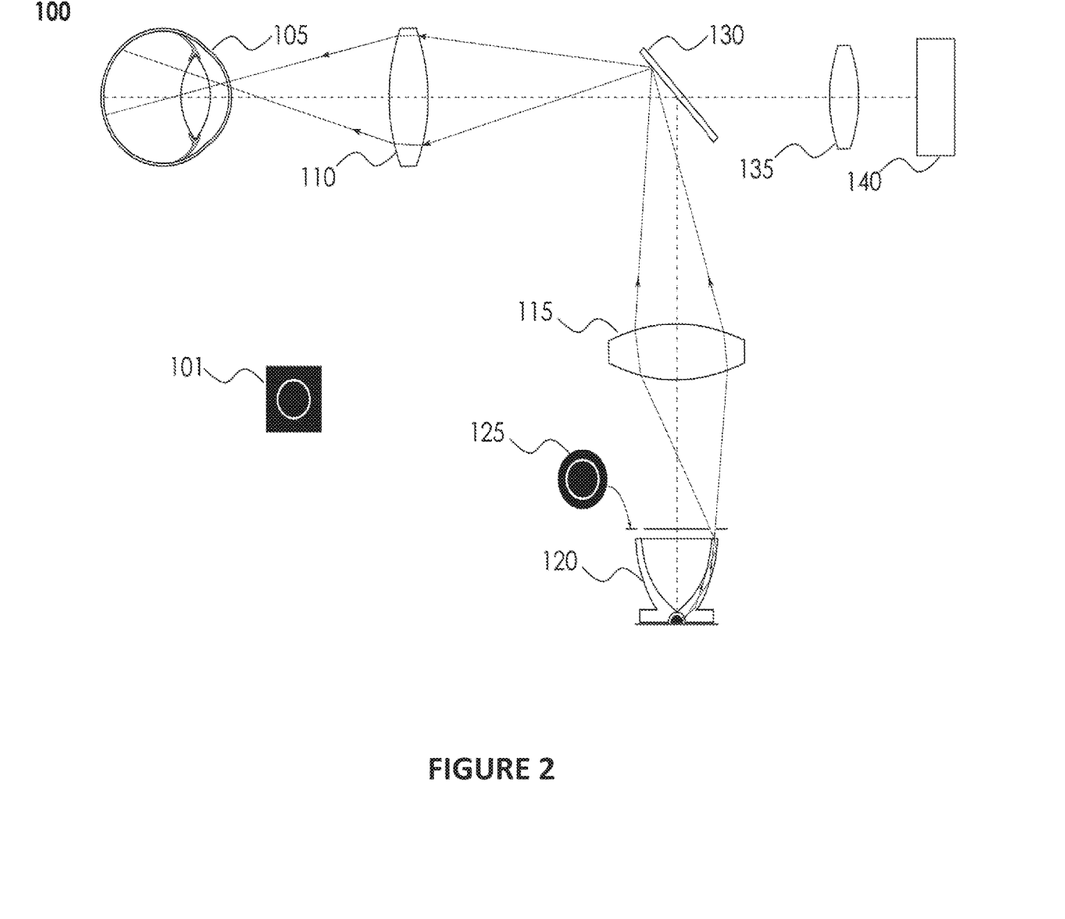
FIG. 2 is a schematic diagram of a Fundus Camera that uses an annular light.

After adjusting the position and the controls of the 140, and the position of the eye 105 of the subject, an image of the uniformly illuminated retina is taken. In certain fundus cameras, while making the adjustments, before taking a photograph of the uniformly illuminated retina, the annular light source 120 may produce an annular beam of light invisible to the human eye, such as infrared light, for example. If light visible to the human eye is used, the pupil of the eye 105 may contract and hinder the capturing of the image by the camera 140. Also, while the human eye is insensitive to infrared light the sensors of digital cameras are sensitive to it. When the digital camera 140 is operated to capture the image by depressing the shutter button, for example, the annular light source 120 may produce a flash of light visible to the human eye. The image of the retina uniformly illuminated by the annular light source is then captured for further analysis by a trained health care provider, such as an ophthalmologist, for example.

Figure 3:
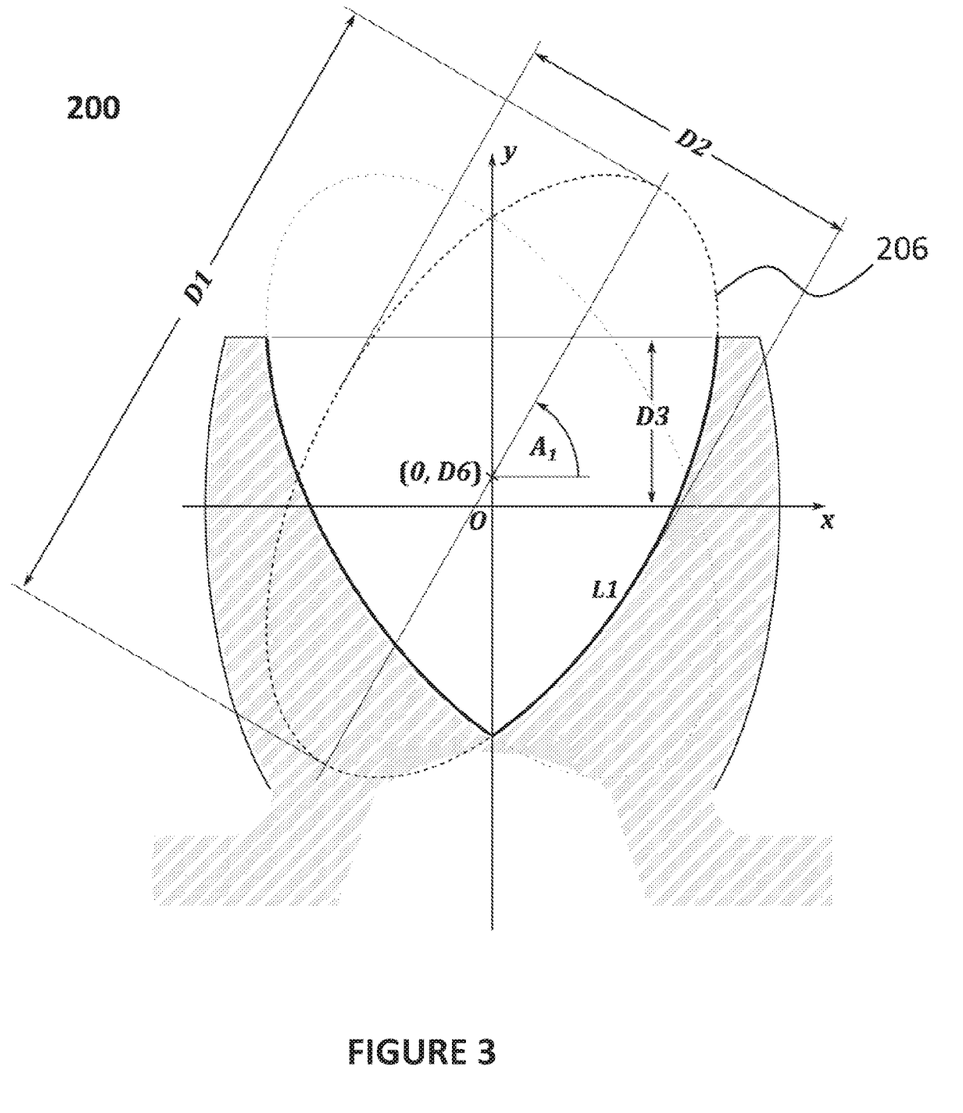
FIG. 3 shows a cross section of the light guide portion according to one embodiment of the present disclosure showing the inner contour of the cross section of the wall of the cup shaped light guide.
Figure 4:
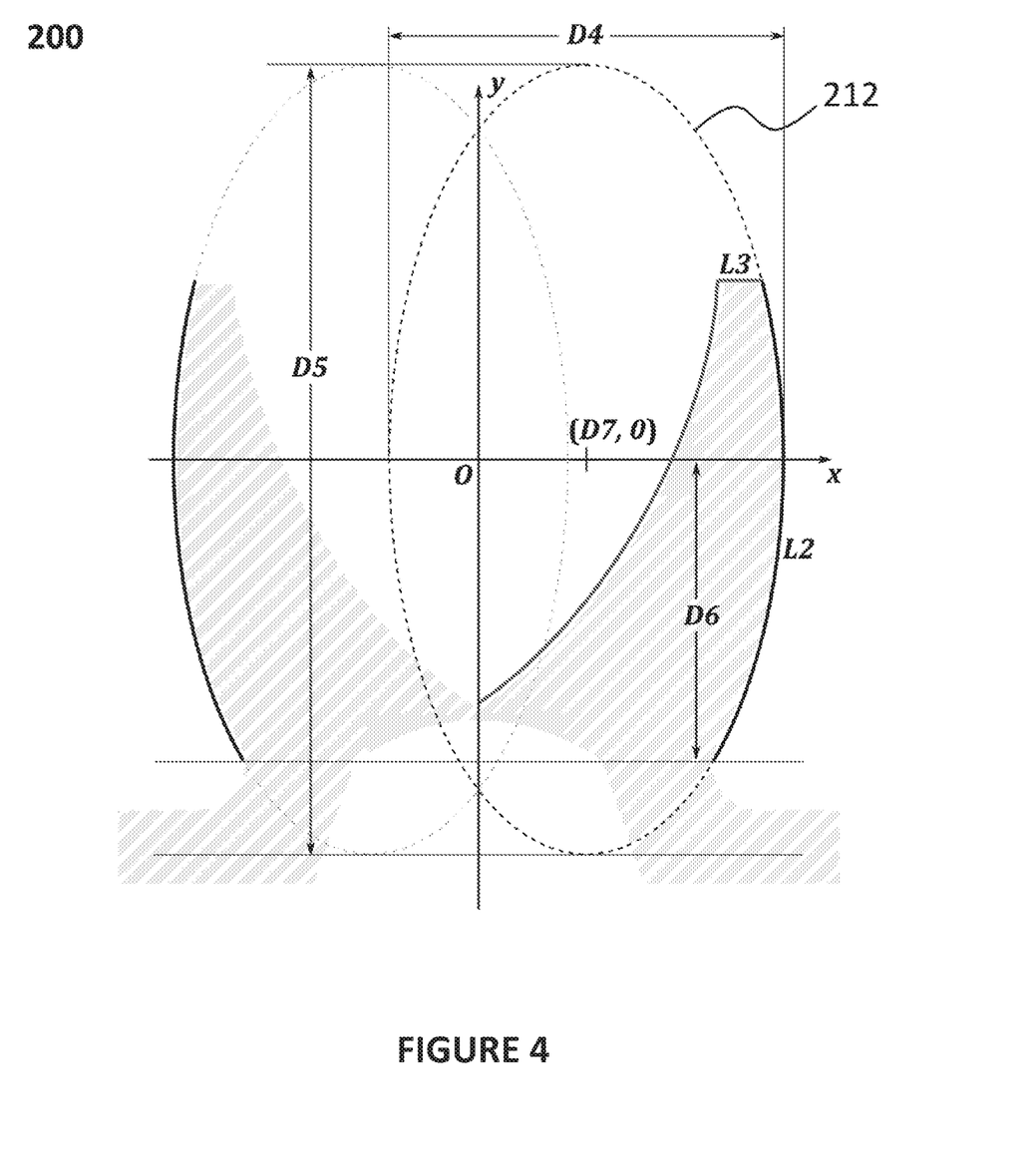
FIG. 4 shows a cross section of the light guide portion according to one embodiment of the present disclosure showing the outer contour of the cross section of the wall of the cup shaped light guide.

With reference to FIGS. 3 and 4, an embodiment of the disclosed annular light source device will be described in general terms and then in particular, as follows. The annular light source device is a single integral device. For the purposes of clear definition and understanding, however, the annular light source device is divided into two portions, conceptually. It is to be noted that this does not mean that there are two separate portions assembled to form a whole. In fact, it is produced by a suitable process, such as injection moulding for instance, as a single integral whole.

The first portion of the device can be described as a cup shaped portion. For the purposes of understanding, the cup is defined with reference to Cartesian coordinates and their origin, wherein the positive Y direction is treated as up. The cup has a wall formed by a clear, colourless, substantially transparent material. The wall of the cup has an inner surface L1 defined by a certain contour and an outer surface L2 defined by another contour. Thus, it suffices to define the cross section of the wall of the cup on the x-y plane. Once the two contours forming the inner surface and the outer surface of the wall are defined, and if this cross section is rotated in three dimensional space around the y-axis, the complete cup shaped portion can be defined and understood by a person skilled in the art.

The annular light source device for producing annular illumination comprises a light guide portion and a light collector portion. The light guide portion is substantially of the shape of a cup. The cup is formed by a wall made of a transparent material. The material could be a clear, substantially transparent, material, polycarbonate, for example. The wall of the cup has a cross section defined with reference to a Cartesian plane and with reference to Cartesian x-axis and y-axis and origin. The cross section has an outer contour and an inner contour. The outer contour of the wall is a section of a first ellipse with its major axis being parallel to the y-axis. The centre of the first ellipse is displaced along the x-axis by a first predetermined distance. The ratio of the length of the major axis and the length of the minor axis of the first ellipse is a first predetermined number. The inner contour of the wall is a section of a second ellipse. The major axis of the second ellipse forms a first predetermined angle with the x-axis and intersects the y-axis at a second predetermined distance from the origin. The ratio of the length of the major axis and the length of the minor axis of the second ellipse is a second predetermined number. The inner contour spans a line parallel to the x-axis at a third predetermined distance and the intersection of the inner contour and the y-axis. The outer contour spans the line parallel to the x-axis at the third predetermined distance and an intersection of the outer contour and a line parallel to the x-axis at a fourth predetermined distance from the origin. The rim of the cup or the annular light portion is defined by a straight line spanning the points of intersection of the outer contour and inner contour and the line parallel to the x-axis at a third predetermined distance.

The contour of the inner surface of the wall of the cup is a section of a first ellipse 206, of predefined dimensions and shown in dotted line. The major axis of the ellipse is at a predefined angle A1 with reference to the x-axis, with the centre of the ellipse 206 having the coordinates of zero and a predefined number (0, D6) corresponding to the x and y coordinates. The numbers represent distance, in a predefined unit of distance, mm for instance. Hereinafter all the distances have the units mm and may not be explicitly stated. The inner surface ends where the section of the ellipse 206 intersects the y-axis and at the other end where it intersects a line parallel to the x-axis at a predefined distance D3, from the origin, along the y-axis.

The contour of the outer surface L2 of the wall of the cup is described with reference to FIG. 4. The contour of the outer surface of the wall of the cup is a section of a second ellipse 212 of predefined dimensions, shown in dotted line and different from the first ellipse 206. The major axis of the second ellipse is parallel to the y-axis. The centre of the second ellipse has predefined coordinates of a predefined number and zero (D7, 0) corresponding to the x and y coordinates wherein the numbers represent distance and are in a predefined unit of distance. The contour of the outer surface L2 ends at the one end where it intersects a line parallel to the x-axis at predefined distance D3 from the origin, on the y-axis. At the other end it ends where it intersects the line parallel to the x-axis at a predefined distance D6, from the origin, on the y-axis. This point is shown as point P.

Thus, as described above, the cross section of the wall of the cup shaped light guide portion defined by lines marked L1, L2 and L3 in FIGS. 3 and 4, when rotated in three dimensional space around the y axis generates the cup shaped light guide portion of the annular light guide device.

What follows is a general description of the portion of the device referred to as the light collector portion. The purpose of the light collector portion is to receive light emitted by a light source, preferably a point light source, such as a light emitting diode, hereinafter, LED, positioned suitably with reference to the annular light source device. The light received by the light collector portion passes through it, enters the light guide portion, undergoes total internal reflection and emerges from the rim L3 of the cup shaped light guide portion described hitherto.

If the light guide portion is treated as being upright, for the sake of conceptual understanding, the light collector portion may be treated as an inverted cup.

Figure 5:
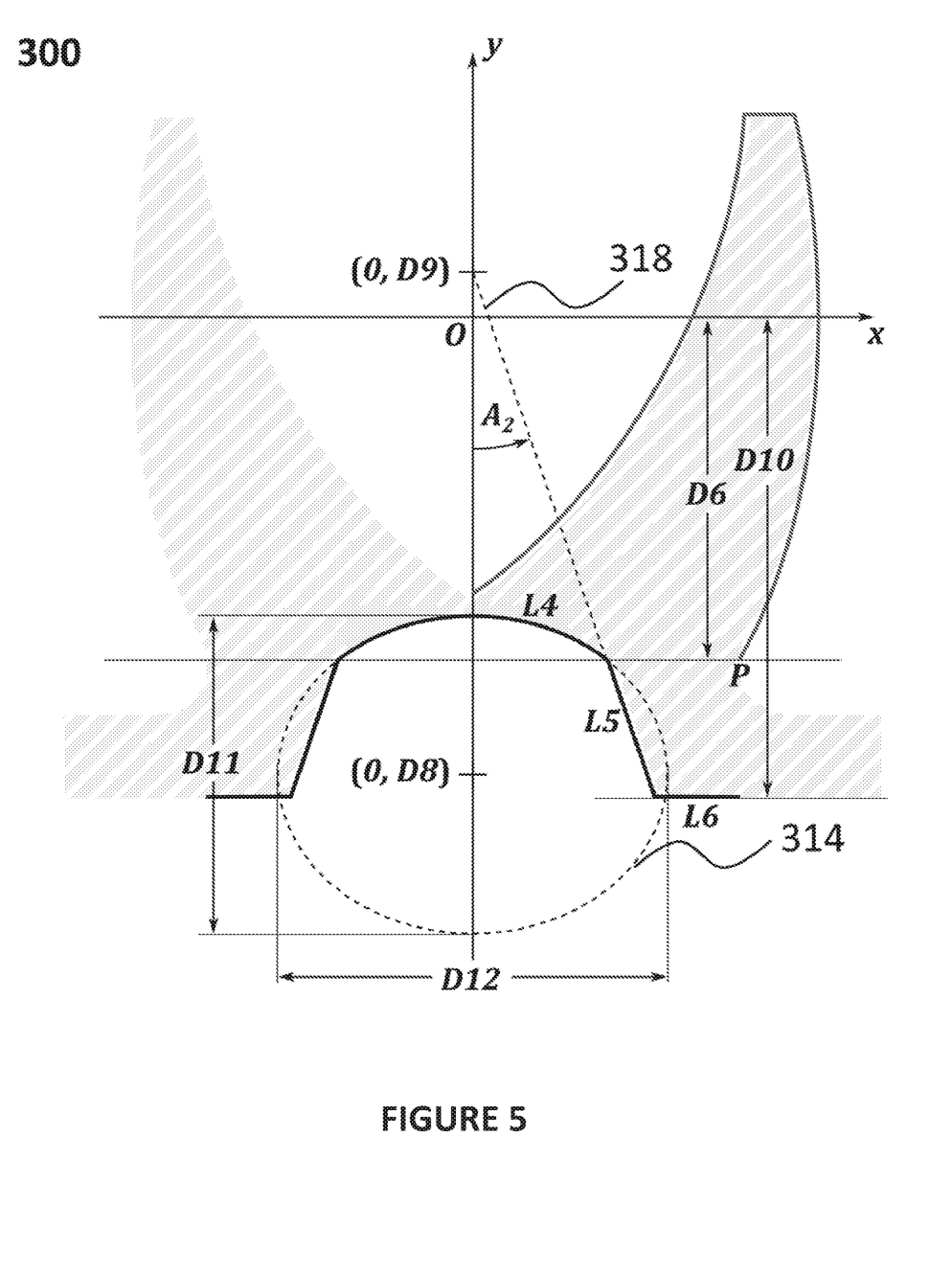
FIG. 5 shows a cross section of the light collector portion of the light guide device, according to one embodiment of the present disclosure.
Figure 6:
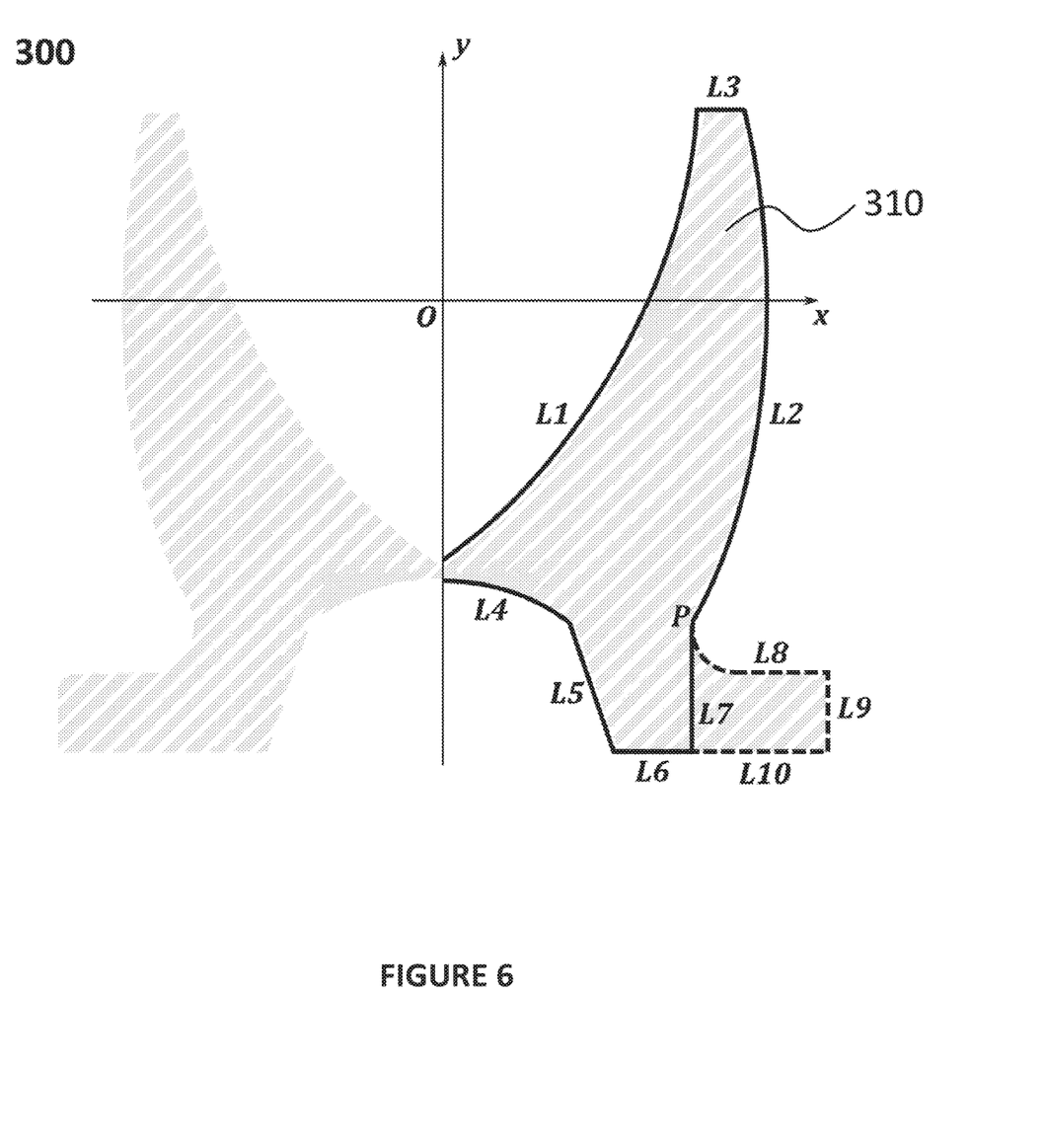
FIG. 6 shows a cross section of the light guide device as an integral whole according to one embodiment of the present disclosure.
Figure 7:
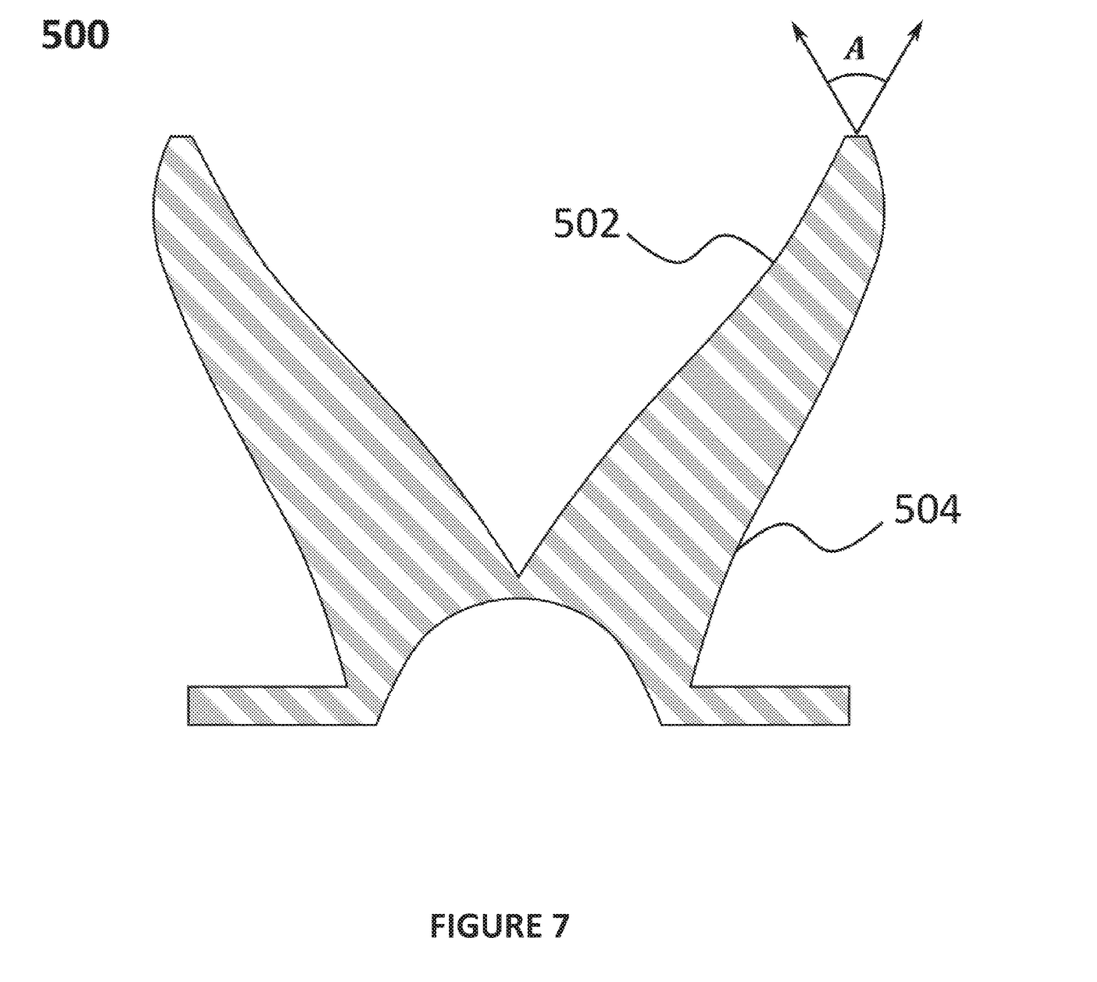
FIG. 7 shows an exemplary variant of the disclosed device the light guide portion with a higher order polynomial defining the contours of the inner and out surfaces of the cup shaped light guide portion, according one embodiment of the present disclosure.

The contours of the surfaces of the wall of the inverted cup may be described as below, with reference to FIG. 5. The contour of the inner surface of the wall of the inverted cup proximal to the origin O of the Cartesian coordinates is a part of a third ellipse of predefined dimensions, with its major axis parallel to the x-axis. The centre of the third ellipse is at a predefined distance from the origin. The position of the centre of the major axis may be defined alternatively as having an x coordinate of zero and a y coordinate of a predefined number. Another contour of the inner surface is the straight line extension of the straight line that intersects the y axis at a predetermined distance from the origin O at a predetermined angle. Another contour of the wall of the inverted cup is a fourth straight line parallel to the x-axis at a predetermined distance from the x-axis as shown in FIG. 5. The last contour of the outer surface of the wall of the inverted cup is a straight line parallel to the y-axis extending from the contour of the outer wall of the cup shaped light guide portion.

It should be noted that the term 'a predetermined distance' is used in the foregoing description are not the same and each time it is used, it may be referring to a distance of a different magnitude and has been used so for ease of understanding.

As in the case of the description of the light guide portion of the annular light source device, the cross section of the wall of the light collector portion of the annular light source device, when rotated in space around the y-axis yields the inverted cup shaped light collector portion of the annular light source device. This portion however may be extended around this shape to enable the provision of features for mounting and such purposes.

The annular light source device is described in detail with greater specificity. For the sake of explanation, the description includes two essential portions, namely, the light guide portion and the light collector portions.

The light collector portion of the annular light source device is meant for collecting the light emitted by a light source, an LED for example. The light collector portion has the shape of an inverted cup. It is integral with the light guide portion and forms the light guide device as a whole. The cross section of the wall of the inverted cup is defined as follows. The contour of an inner surface L4 of the inverted cup proximal to the origin is a section of a third ellipse 314 with its major axis parallel to the x-axis. The ratio of the length of the major axis and the length of the minor axis of the third ellipse is a third predetermined number. The centre of the third ellipse lies on the y-axis at a fifth predetermined distance from the origin. The coordinates of this centre may be defined as (0, D8). The inner contour L5 of the cross section of the wall of inverted cup is a part of a straight line 318 intersecting the y-axis at a sixth predetermined distance (0, D9) from the origin at a second predetermined angle A2 with the y-axis. L5 spans the point of intersection of line 318 with the third ellipse and the point of intersection of line 318 with a line parallel to the x-axis at a seventh predetermined distance D10 from the x-axis. The contour of the inner surface IA spans the point of intersection of the third ellipse and line 318 and the point of intersection of the third ellipse 314 and the y-axis. The outer contour L6 of the inverted cup is a straight line parallel to the x-axis. It spans the point of intersection of line 318 and the line parallel to the x-axis at a seventh predetermined distance (D10) from it and a line through point P parallel to the y-axis. This line, parallel to the y-axis, from point P to the point of intersection with L6 is shown as L7 and forms the outer contour of the inverted cup of the light collector portion.

It is to be noted that the part of the light collector portion bounded by L5, L6, and L7 is the preferred minimum part of the light collector portion of the disclosed light guide device, in view of the functions of light collection and light guide to produce an annular illumination. For the purposes of mounting the disclosed device in a fundus camera, however, the portion of the disclosed light guide device may be extended as required by the designer of a light guide device designing a device based on the present disclosure. The designer may extend this portion based on the requirements of mechanical mounting and injection moulding and other such requirements. An exemplary extension of this portion is shown in figure indicated in dotted line as L8, L9, and L10.

As described before, this cross section of the wall of the inverted cup is rotated 360° in space around the x-axis, yields the shape of the disclosed inverted cup shaped light collector portion of the annular light source device.

It is to be noted that the wall of the light collector portion has to, primarily, have the features described hitherto. Suitable extensions to it, however, over and above what is described hitherto and shown in FIG. 4 may be or may have to be made to enable mounting it suitably into a fundus camera and the associated hardware.

The clear, colourless, substantially transparent material used to manufacture the annular light source device may be glass or polycarbonate, for instance. The choice of glass, however, poses many impediments to its use to produce the described annular light source. Some of them are: Glass is expensive. It may also have the disadvantage of weight, which necessitated special mounting arrangements. Glass is also difficult to form into the shape described hitherto. Glass is brittle and may shatter on falling and hence requires special handling.

A material that is suitable for producing the annular light source device is Polycarbonate. Polycarbonate lends itself to injection moulding, a process that is very well known and easily adopted for the purpose. It is also lighter than glass and hence it can be mounted with ease in the fundus camera without needing special mounting arrangements. It is also relatively inexpensive vis-à-vis glass. It is also less brittle and does not require special precautions while transporting the individual device, from the manufacturer of the device to the assembler of the fundus camera, for instance.

The annular light source device described hitherto requires a light source, the light emitted by which is formed into an annular light by the light guide portion, through Total Internal Reflection, the light having been collected by the light collector portion of the annular light source device. The light source is preferably a light emitting diode LED. The LED is placed in a location with respect to the annular light source device such that substantially all the light emitted by the LED is collected by the light collector portion of the annular light source device. Further in a preferred embodiment, the LED has a large angle of radiation. In a particularly advantageous embodiment, the angle of radiation of the LED is substantially equal to 120 degrees mechanical. LEDs are available that have a specified nominal angle of radiation. The particularly advantageous embodiment employs an LED whose nominal an angle of radiation is to 120 degrees mechanical. Even though the description above refers to an LED, it is to be understood that it is merely a preferred light source and any light source with a low form factor and a large divergence angle, preferably as close to 120° as possible, will suffice. Such light sources are also covered under the scope of this disclosure.

It is to be noted that the disclosed annular light source device has been described with the cross section of the wall of the cup shaped light guide portion being formed by sections of ellipses disposed in the described relationships. It is not necessary that the curves be ellipses. It is, in fact, an advantageous implementation of the principle of defining the cross section of the wall of the cup shaped light guide with suitable curves. The possible curves could be parabolas, exponential curves with appropriate exponents of the universal constant e. Still further, the sections of curves used to describe the contours of the walls of the cup shaped light guide portion need not be curves that can be defined by a second order equation. A higher order polynomial may also be used to describe the surface. With such contours, defined by a higher order polynomials, it is possible to get annular light sources with larger diameters without changing the size of the part considerably. This could also help in achieving desired beam divergence A at exit point of the waveguide.

FIG. 5 shows an annular light source with the contours of the walls of the cup shaped light guide portion having inner wall 502 and outer wall 504 defined by a higher order polynomial. The figure indicates the rim of the cup shaped annular light source device and shows the angle A at which the light emanates from it.

Further, even though the inventors solved the technical problems in the field of a fundus camera in particular, it is to be noted the disclosed concept may also be used in other ophthalmic diagnostic instruments. For example, further embodiments of the disclosed concept with suitable modifications, if necessary, may be used in auto refractometers. Auto refractometers are diagnostic instruments used for testing the defects in human eyes such as myopia short sight, long sight hyperopia or presbyopia and astigmatism. Auto refractometers are used in what is, in layman's language referred to as, computerised eye testing or objective eye testing. Alternatively, they may be employed in lens meters for measuring the properties of lenses. They may also be employed in refractometers that is to say instruments used for the measurement of the refractive indices of liquids.

Still further, the annular light sources produced based on the disclosed principle may be used in special purpose decorative illumination.

In general, the proposed solution may be applied in various applications, including those not related to fundus cameras and other ophthalmic instruments.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also; those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

I claim:

1. A light guide device, for producing annular illumination, the device comprising:
   a light guide portion
   having substantially the shape of a cup formed by a wall made of a substantially transparent material, wherein,
   the wall having a cross section defined by a Cartesian plane and with reference to Cartesian x-axis and y-axis and origin;
   the cross section having an outer contour and an inner contour;
   the outer contour of the wall being a section of a first ellipse with its major axis being parallel to the y-axis with a centre of the first ellipse displaced along the x-axis by a first predetermined distance, wherein a ratio of a length of a major axis and a length of a minor axis of the first ellipse is a first predetermined number;
   the inner contour of the wall being a section of a second ellipse with its major axis forming a first predetermined angle with the x-axis and intersecting the y-axis at a second predetermined distance from the origin, wherein a ratio of a length of a major axis and a length of a minor axis of the second ellipse is a second predetermined number;
   the inner contour spanning a line parallel to the x-axis at a third predetermined distance and the intersection of the inner contour and the y-axis;
   the outer contour spanning the line parallel to the x-axis at the third predetermined distance and an intersection of the outer contour and a line parallel to the x-axis at a fourth predetermined distance from the origin;
   an annular light portion defined by a straight line spanning the points of intersection of the outer and inner contours and the line parallel to the x-axis at the third predetermined distance; and
   a light collector portion for collecting a light emitted by a light source, the light collector portion having a shape of an inverted cup integral with the light guide device, wherein a cross section of a wall of the inverted cup is characterised by:
   a contour of an inner surface of the inverted cup proximal to the origin being a section of a third ellipse with its major axis parallel to the x-axis, with the centre of the third ellipse lying on the y-axis at a fifth predetermined distance from the origin and spanning a point of intersection of the third ellipse and the y-axis and the line parallel to the x-axis at the fourth predetermined distance, the ratio of a length of a major axis and a length of a minor axis of the third ellipse being a third predetermined number;
   an inner contour of the cross section of the inverted cup being a part of a straight line intersecting the y-axis at a sixth predetermined distance from the origin at a second predetermined angle with the y-axis, and extending between a point of intersection with the section of the third ellipse a point of intersection with a line parallel to the x-axis at a seventh predetermined distance from it; and the outer contour of the inverted cup being a straight line parallel to the y-axis, spanning a point of intersection of the line parallel to the x-axis at the fourth predetermined distance from it and the outer contour of the light guide.

2. The light guide device of claim 1, wherein the substantially transparent material of the light guide device is one of polycarbonate or glass.

3. The light guide device of claim 1, wherein the first predetermined number is in the range of 1.75 and 2.25, the second predetermined number is in the range of 1.65 and 2.15, the first predetermined distance is in the range of 2.4 and 2.8 units, the second predetermined distance is in the range of 0.5 and 1.0 units, the third predetermined distance is in the range of 4.0 and 4.6 units, and the fourth predetermined distance is in the range of 7.0 and 7.5 units.

4. The light guide device of claim 1, wherein the first predetermined number is in the range of 1.95 and 2.05, the second predetermined number is in the range of 1.8 and 2.0, the first predetermined distance is in the range of 2.5 and 2.7 units, the second predetermined distance is in the range of 0.7 and 0.8 units, the third predetermined distance is in the range of 4.2 and 4.4 units, and the fourth predetermined distance is in the range of 7.2 and 7.35 units.

5. The light guide device of claim 1, wherein the third predetermined number is in the range of 1.1 to 1.3, the fifth predetermined distance is in the range of 9.5 and 10.0, the sixth predetermined distance is in the range of 0.8 and 1.1, the seventh predetermined distance is in the range of 10.0 and 10.4, and the second predetermined angle is in the range of 18 degrees and 20 degrees.

6. The light guide device of claim 1, wherein the third predetermined number is in the range of 1.2 to 1.25, the fifth predetermined distance is in the range of 9.6 and 9.8, the sixth predetermined distance is in the range of 0.8 and 1.1, the seventh predetermined distance is in the range of 10.1 and 10.3, and the second predetermined angle is in the range of 18.5 degrees and 19.5 degrees.

7. The light guide device of claim 1, wherein an annular disc integral to it, with a thickness in the range of 1.6 and 2.0 units, extends radially for enabling an assembly of the light guide device.

8. An annular light source system, comprising:
the light guide device of claim 1; and
the light source for generating an annular illumination, wherein the light guide device is assembled, wherein the light source for generating the annular illumination is positioned inside a cavity of the inverted cup like light collector portion with an axis of the light emanated by the light source lies substantially along the y-axis of a reference Cartesian coordinates and a direction of radiation of the light source is towards the origin of the reference Cartesian coordinates.

9. The annular light source system of claim 8, wherein the light source is substantially a point light source.

10. The annular light source system of claim 9, wherein the light source is substantially the point light source having an angle of radiation between 100 degrees and 150 degrees.

11. The annular light source system of claim 9, wherein the light source is a light emitting diode.

12. The annular light source system of claim 10, wherein the light source is a light emitting diode with an angle of radiation and preferably a light emitting diode having an angle of radiation substantially equal to 120 degrees.

13. An ophthalmic instrument comprising an annular light source system of claim 8.

* * * * *